United States Patent
Dalal et al.

(10) Patent No.: US 8,634,930 B2
(45) Date of Patent: Jan. 21, 2014

(54) SYSTEM FOR PROVIDING DIABETIC THERAPY

(75) Inventors: Yousufali Dalal, St. Louis Park, MN (US); Andrew P. Kramer, Stillwater, MN (US); Lizbeth M. Mino, Salt Lake City, UT (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1419 days.

(21) Appl. No.: 11/428,070

(22) Filed: Jun. 30, 2006

(65) Prior Publication Data

US 2008/0004672 A1 Jan. 3, 2008

(51) Int. Cl.
*A61N 1/36* (2006.01)

(52) U.S. Cl.
USPC .......... 607/115; 607/22; 600/365; 600/347

(58) Field of Classification Search
USPC ............. 607/2–6, 9, 18, 22, 44, 118, 40, 62; 600/316, 319, 365, 513, 517, 347; 604/891.1, 500, 503–505, 65–67, 604/890.1
See application file for complete search history.

(56) References Cited

U.S. PATENT DOCUMENTS

| 5,199,428 | A | 4/1993 | Obel et al. |
| 5,231,988 | A | 8/1993 | Wernicke et al. |
| 5,741,211 | A * | 4/1998 | Renirie et al. ............. 600/300 |
| 6,615,081 | B1 | 9/2003 | Boveja |
| 6,740,072 | B2 * | 5/2004 | Starkweather et al. ....... 604/504 |
| 6,832,114 | B1 | 12/2004 | Whitehurst et al. |
| 7,069,078 | B2 | 6/2006 | Houben |
| 7,277,761 | B2 | 10/2007 | Shelchuk |
| 2004/0199210 | A1 * | 10/2004 | Shelchuk ................. 607/17 |
| 2004/0249416 | A1 | 12/2004 | Yun et al. |
| 2005/0065553 | A1 * | 3/2005 | Ben Ezra et al. ........... 607/2 |
| 2005/0143779 | A1 * | 6/2005 | Libbus ..................... 607/9 |
| 2005/0182389 | A1 | 8/2005 | LaPorte et al. |
| 2006/0085045 | A1 * | 4/2006 | Harel et al. ............... 607/40 |
| 2007/0213657 | A1 * | 9/2007 | Jennewine et al. ......... 604/66 |

OTHER PUBLICATIONS

Apstein, C. S., "Glucose-Insulin-Potassium for Acute Myocardial Infraction", *Circulation*, vol. 98, (1998), 2223-2226.
Grossman, E., et al., "Diabetic and Hypertensive Heart Disease", *Annuals of Internal Medicine*, 125(4), (1996), 304-310.
Lopaschuk, G., "Metabolic Abnormalities in the Diabetic Heart", *Heart Failure Reviews*, 7(2), (2002), 149-59.

(Continued)

*Primary Examiner* — Carl H Layno
*Assistant Examiner* — Erica Lee
(74) *Attorney, Agent, or Firm* — Schwegman Lundberg & Woessner, P.A.

(57) ABSTRACT

Various system embodiments include a glucose control input, a low physical activity input, and a diabetic therapy delivery system adapted to respond to the glucose control input and the low physical activity input to deliver diabetic therapy. According to various embodiments, the diabetic therapy includes an anti-arrhythmia therapy, a hypertension therapy, a neural stimulation therapy adapted to reduce a risk of myocardial infarction, a neural stimulation therapy adapted to be applied after a myocardial infarction to reduce an infarct area, a neural stimulation therapy adapted to reduce a risk of sudden cardiac death, a therapy adapted to secrete insulin, or a therapy to reduce a workload of a diabetic heart. Other aspects and embodiments are provided herein.

42 Claims, 10 Drawing Sheets

(56) References Cited

OTHER PUBLICATIONS

"Diabetes and Exercise", [online]. [retrieved Sep. 21, 2011]. Retrieved from the Internet: <URL: http://www.uihealthcare.com/topics/diabetes/diabetesandexercise.html>, (2011), 4pgs.

"Tight Diabetes Control", © 1995-2011, American Diabetes Association. [retrieved Sep. 21, 2011]. Retrieved from the Internet: <URL: http://www.diabetes.org/living-with-diabetes/treatment-and-care/blood-glucose-control/tight-diabetes-control.html>, (2011), 4 pgs.

* cited by examiner

SYSTEM FOR PROVIDING DIABETIC THERAPY

FIELD

This application relates generally to medical devices and, more particularly, to systems, devices and methods for providing diabetic therapy.

BACKGROUND

Diabetic autonomic neuropathy alters heart rate control (tachy) and vascular function (dilation of vasculature). Also, it has been reported that the incidence and severity of angina, acute myocardial infarction, and congestive heart failure is greater for diabetics than non-diabetic patients.

A healthy heart produces a constant and plentiful supply of adenosine triphosphate (ATP), an energy molecule required for cells to function. ATP is primarily produced by the metabolism of carbohydrates, fatty acids and proteins. The primary metabolized carbohydrate is glucose, which is a more efficient energy source for the heart than fatty acids as fatty acids require approximately 10% more oxygen to produce an equivalent amount of ATP.

Diabetes can change cardiac energy metabolism, which can contribute to reduced cardiac contractility and ischemic injury. For a healthy heart, fatty acid oxidation typically provides 60 to 70% of the ATP but can provide 90 to 100% of the ATP for patients with uncontrolled diabetes. Thus, diabetic hearts work harder, demand more oxygen and make the heart prone to ischemia and arrhythmias. Myocardial metabolic alterations can cause increased asymptomatic ischemia, acute myocardial infarction, reduced survival post myocardial infarction, and changes in the excitation-contraction coupling of the myocardium thereby leading to diabetic cardiomyopathy.

SUMMARY

Various aspects of the present subject matter relate to a system. Various system embodiments include a glucose control input, a low physical activity input, and a diabetic therapy delivery system adapted to respond to the glucose control input and the low physical activity input to deliver diabetic therapy. According to various embodiments, the diabetic therapy includes an anti-arrhythmia therapy. According to various embodiments, the diabetic therapy includes a hypertension therapy. According to various embodiments, the diabetic therapy includes a neural stimulation therapy adapted to reduce a risk of myocardial infarction. According to various embodiments, the diabetic therapy includes a neural stimulation therapy adapted to be applied after a myocardial infarction to reduce an infarct area. According to various embodiments, the diabetic therapy includes a neural stimulation therapy adapted to reduce a risk of sudden cardiac death. According to various embodiments, the diabetic therapy includes a therapy adapted to secrete insulin.

According to various embodiments, the diabetic therapy is adapted to reduce a workload of a diabetic heart. As used herein, the term workload relates to the energetic or metabolic workload of the heart. Terms such as preload, afterload, and contractility relate to the mechanical or hemodynamic workload of the heart. The metabolic workload is related to the mechanical or hemodynamic workload of the heart, as metabolism supplies the energy required to perform the mechanical work. As will be understood to those of ordinary skill in the art upon reading and comprehending this disclosure, the metabolic workload encompasses more than the hemodynamic workload. For example, the metabolic workload also supplies the energy to support the growth process of cardiac tissue. Various embodiments reduce ventricular contractility of a diabetic heart to reduce the workload. Various embodiments reduce norepinephrine release to attenuate ventricular remodeling of a diabetic heart to reduce the workload. Various embodiments reduce induce coronary artery vasodilation to reduce the workload. Various embodiments reduce arterial peripheral resistance to reduce the workload. Various embodiments stimulate insulin release to promote glucose uptake and metabolism to reduce the workload. Various embodiments pace myocardia to unload a diabetic heart and reduce the workload.

Various aspects of the present subject matter relate to a method. Various method embodiments include determining if a diabetic patient has poor glucose control, determining when the diabetic patient is experiencing a period of low physical exertion, and delivering diabetic therapy when the diabetic patient has poor glucose control and is experiencing the period of low physical exertion.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1A:
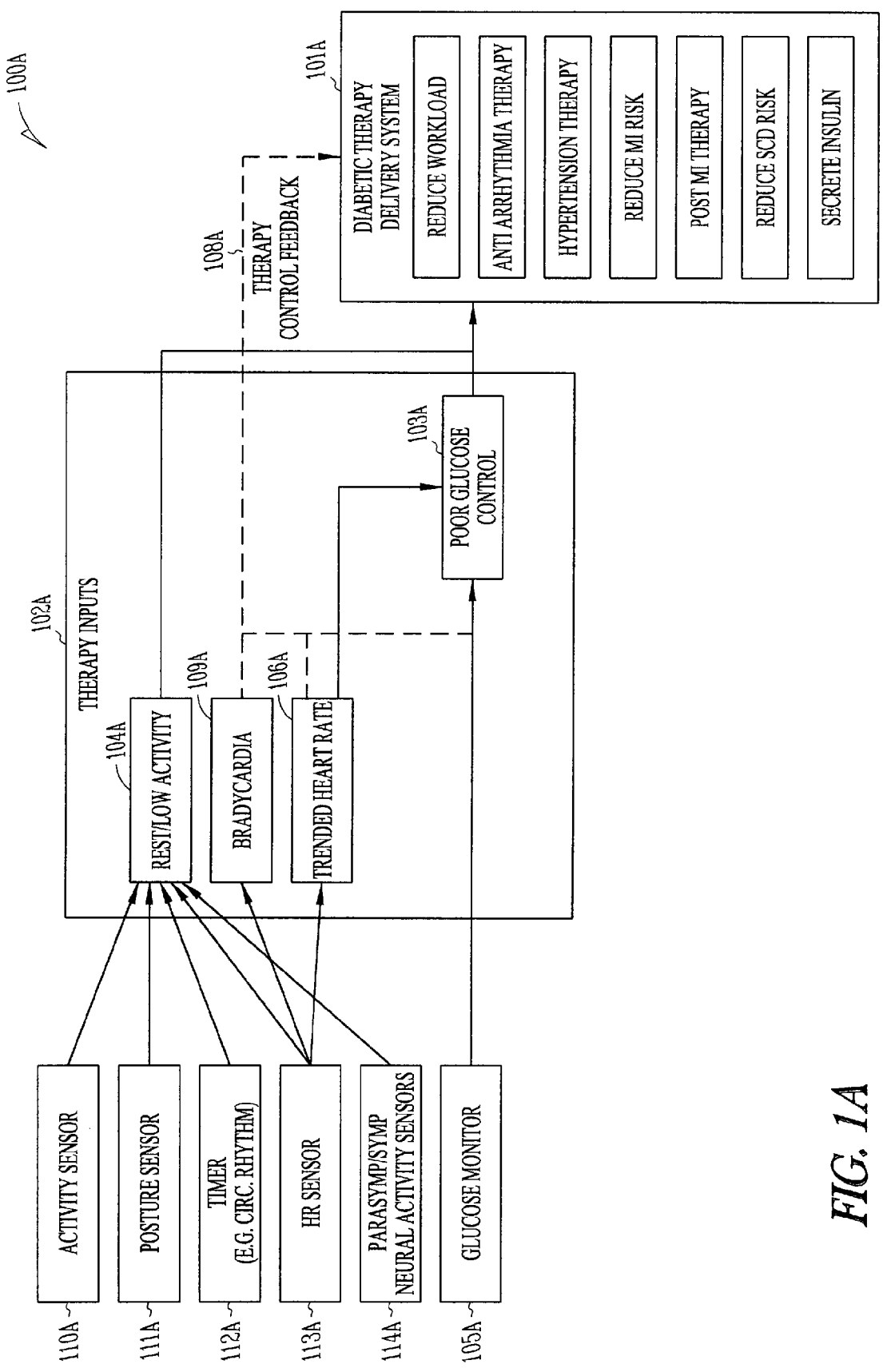
FIG. 1A illustrates an embodiment of a system for delivering diabetic therapy.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter includes a diabetic therapy. Various diabetic therapy embodiments unload the heart during periods of rest to ameliorate the heart disease. Various embodiments slow the heart to relieve the workload and prevent the heart from demanding more energy than can be supplied and entering a hypoxic state. The present subject matter can control the metabolic demand until the ATP stores are regenerated. Various diabetic therapy embodiments provide an antiarrhythmia therapy, a hypertension therapy, a prophylactic therapy to reduce a risk of a myocardial infarction (MI), a therapy to reduce a size of an infarct following an MI, a prophylactic therapy to reduce a risk associated with sudden cardiac death (SCD), and a therapy to secrete insulin. Any one or combinations of two or more of these therapies can be implemented, according to various embodiments of the present subject matter.

Various embodiments slow the heart rate down by stimulating a neural target to elicit an appropriate parasympathetic response. Various embodiments stimulate a neural target to stimulate parasympathetic activity and/or inhibit sympathetic activity to slow the heart rate. Some embodiments stimulate an efferent neural pathway and some embodiments stimulate an afferent neural pathway. Various embodiments use selective vagal stimulation to slow the heart rate. Various embodiments stimulate a neural target to elicit a parasympathetic response to reduce a sympathetic tone for the heart. Various embodiments stimulate a target, such as a vagus nerve, to secrete insulin.

Diabetic patients measure their blood glucose levels using Blood Glucose Monitor (BGM or GM). Many GMs are Bluetooth enabled, such that glucose measurements and trends from them can be sent to other devices. Various embodiments send data to a diabetic therapy device, such as an Implantable Medical Device (IMD), when glucose levels are out of range and the patient is not having the appropriate insulin response. With this alert the diabetic therapy device delivers therapy when the glucose levels are not controlled. Sensed glucose levels can be used to enable a therapy (e.g. enable a therapy when glucose levels are high) or titrate a therapy (e.g. reduce or terminate a therapy when glucose levels are low). States of rest or inactivity can be determined using measurements from an activity sensor (e.g. accelerometer), a physiological sensor (e.g. minute ventilation sensor), and/or posture sensor. Once rest is detected, therapy is applied to slow the heart as patients may most tolerate lowered heart rates at times of rest or low physical exertion.

Various embodiments stimulate a neural target to provide a local response for the diabetic therapy. For example, the neural target can be chosen to slow a heart rate, to reduce sympathetic tone, to reduce blood pressure, or to encourage insulin secretion. Some embodiments selectively stimulate desired neural pathways in a nerve without stimulating other neural pathways. Some embodiments selectively stimulate cardiac nerve branches to provide a more local effect. Various embodiments stimulate a neural target to provide a more global parasympathetic response. In various embodiments, the neural target includes a vagus nerve. A more global stimulation of the vagus nerve may promote the release of insulin into the patient's system which may be beneficial for their diabetic control. Some embodiments provide selective neural stimulation to promote insulin secretion in addition to stimulation to reduce heart rate. Some embodiments include an insulin pump for use in improving glucose control.

The discussion that follows is organized into a brief discussion of physiology, a discussion of diabetic therapy embodiments and device/system embodiments used to implement diabetic therapy, and a brief discussion of other therapies that can be combined or integrated with the diabetic therapy.

Physiology

Various embodiments use neural stimulation to slow the heart rate for a diabetic patient with poor glucose control. To assist a reader in understanding the disclosed subject matter, a brief discussion of hypertension, heart failure (HF), cardiac remodeling and the nervous system is provided below.

Hypertension

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

Hypertension can cause structural and functional cardiac abnormalities that lead to myocardial infarction, congestive heart failure, and sudden cardiac death. Patients with diabetes and hypertension have a higher incidence of coronary artery disease than do patients with diabetes or hypertension alone. Diabetes appears to reduce post-MI survival, increase ischemic myocardial events, and increase sudden death caused by ventricular arrhythmias. The combination of diabetes and hypertension often lead to premature congestive heart failure, sudden cardiac death, and acute myocardial infarction.

Heart Failure, Cardiac Remodeling and HF Status Parameters

Heart failure refers to a clinical syndrome in which altered cardiac function leads to a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality.

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the ventricular preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

HF status parameters, such as autonomic balance indicators (ABIs) which may detect the reduced autonomic balance of HF patients, can be used to determine when a diabetic patient has poor glucose control and when to provide therapy for the diabetic heart. Examples of parameters that can be used to determine HF status include heart rate variability (HRV), heart rate turbulence (HRT), heart sounds, electrogram features, activity, respiration, and pulmonary artery pressure. These parameters are briefly discussed below.

Measure of HRV have been proposed to assess autonomic balance. HRV relates to the regulation of the sinoatrial node, the natural pacemaker of the heart by the sympathetic and parasympathetic branches of the autonomic nervous system. An assessment of HRV is based on the assumption that the beat-to-beat fluctuations in the rhythm of the heart provide us with an indirect measure of heart health, as defined by the degree of balance in sympathetic and vagus nerve activity. The time interval between intrinsic ventricular heart contractions changes in response to the body's metabolic need for a change in heart rate and the amount of blood pumped through the circulatory system. For example, during a period of exercise or other activity, a person's intrinsic heart rate will generally increase over a given period of time. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system on blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform ("FFT") techniques, so that its spectral frequency components can be analyzed and divided into low and high frequency bands. For example, the low frequency (LF) band can correspond to a frequency ("f") range $0.04$ Hz$\leq$f$\leq$$0.15$ Hz, and the high frequency (HF) band can correspond to a frequency range $0.15$ Hz$\leq$f$\leq$$0.40$ Hz. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required. One example of a HRV parameter is SDANN (standard deviation of averaged NN intervals), which represents the standard deviation of the means of all the successive 5 minutes segments contained in a whole recording. Other HRV parameters can be used.

HRT is the physiological response of the sinus node to a premature ventricular contraction (PVC), consisting of a short initial heart rate acceleration followed by a heart rate deceleration. HRT has been shown to be an index of autonomic function, closely correlated to HRV, and is believed to be due to the autonomic baroreflex. The PVC causes a brief disturbance of the arterial blood pressure (low amplitude of the premature beat, high amplitude of the ensuing normal beat), which instantaneously responds in the form of HRT if the autonomic system is healthy, but is either weakened or missing if the autonomic system is impaired. By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\ \% = \frac{(RR_{+1} + RR_{+2}) - (RR_{-2} + RR_{-1})}{(RR_{-2} + RR_{-1})} * 100.$$

$RR_{-2}$ and $RR_{-1}$ are the first two normal intervals preceding the PVC and $RR_{+1}$ and $RR_{+2}$ are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application. Rules or criteria can be provided for use to select PVCs and for use in selecting valid RR intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none of the beats are PVCs. One HRT process, for example, excludes RR intervals that are less than a first time duration, that are longer than a second time duration, that differ from a preceding interval by more than a third time duration, or that differ from a reference interval by a predetermined amount time duration or percentage. In an embodiment of such an HRT process with specific values, RR intervals are excluded if they are less than 300 ms, are more than 2000 ms, differ from a preceding interval by more than 200 ms, or differ by more than 20% from the mean of the last five sinus intervals. Various embodiments of the present subject matter provide programmable parameters, such as any of the parameters identified above, for use in selecting PVCs and for use in selecting valid RR intervals before and after the PVCs. Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Heart sounds can be used in determining a heart failure status. Distinguishable heart sounds include the following four heart sounds. The first heart sound ($S_1$), is initiated at the onset of ventricular systole and consists of a series of vibrations of mixed, unrelated, low frequencies. $S_1$ is chiefly caused by oscillation of blood in the ventricular chambers and vibration of the chamber walls. The intensity of $S_1$ is primarily a function of the force of the ventricular contraction, but also of the interval between atrial and ventricular systoles. The second heart sound ($S_2$), which occurs on closure of the semi-lunar valves, is composed of higher frequency vibrations, is of shorter duration and lower intensity, and has a more "snapping" quality than the first heart sound. The second sound is caused by abrupt closure of the semi-lunar valves, which initiates oscillations of the columns of blood and the tensed vessel walls by the stretch and recoil of the closed valve. The third heart sound ($S_3$), which is more frequently heard in children with thin chest walls or in patients with rapid filling wave due to left ventricular failure, consists of a few low intensity, low-frequency vibrations. It occurs in early diastole and is believed to be due to vibrations of the ventricular walls caused by abrupt acceleration and deceleration of blood entering the ventricles on opening of the atrial ventricular valves. A fourth or atrial sound ($S_4$), consisting of a few low-frequency oscillations, is occasionally heard in normal individuals. It is caused by oscillation of blood and cardiac chambers created by atrial contraction. Accentuated $S_3$ and $S_4$ sounds may be indicative of certain abnormal conditions and are of diagnostic significance. For example, a more severe HF status tends to be reflected in a larger $S_3$ amplitude.

An electrogram (ECG) can be used as an indicator of heart damage. Examples of ECG features that can be extracted to provide an indicator of heart damage include a QRS complex duration due to left bundle branch block, ST segment deviation, and a Q wave due to myocardial infarction. Any one or combination of these features can be used to provide the indicator of heart damage. Other features can be extracted from the ECG.

Inactive heart failure patients can have a high sympathetic tone as a result of their pathology. Activity sensors can be used to assess the activity of the patient. Sympathetic activity naturally increases in an active patient, and decreases in an inactive patient. Thus, activity sensors can be used to assess the activity of the patient and provide a contextual measurement for use in determining the autonomic balance of the patient, and thus the HF status of the patient. Various embodiments, for example, provide a combination of sensors to trend heart rate and/or respiration rate to provide an indicator of activity.

Two methods for detecting respiration involve measuring a transthoracic impedance and minute ventilation. Respiration parameters, for example, can be derived from a minute ventilation signal and a fluid index can be derived from transthoracic impedance. For example decreasing thoracic impedance reflects increased fluid buildup in lungs, and indicates a progression of heart failure. Respiration can significantly vary a minute ventilation. The transthoracic impedance can be totaled or averaged to provide an indication of fluid buildup. Respiration can be an indicator of activity, and can provide an explanation of increased sympathetic tone that does not directly related to a HF status. For example, it may not be appropriate to change a HF therapy due to a detected increase in sympathetic activity attributable to exercise. Respiration measurements (e.g. transthoracic impedance) can also be used to measure Respiratory Sinus Arrhythmia (RSA). RSA is the natural cycle of arrhythmia that occurs through the influence of breathing on the flow of sympathetic and vagus impulses to the sinoatrial node. The rhythm of the heart is primarily under the control of the vagus nerve, which regulates heart rate and the force of contraction. The vagus nerve activity is dampened and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle.

Pulmonary artery pressure can be used as an indicator of HF. As identified above, high blood pressure can contribute to heart failure. Chronically high blood pressure, or a chronic blood pressure that trends higher, provides an indication of an increased likelihood of heart failure. Various embodiments use pulmonary artery pressure to approximate filling pressure. Filling pressure is a marker of preload, and preload is an indicator of heart failure status.

Nervous System

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force of contraction is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with various tachy arrhythmias including ventricular tachycardia and atrial fibrillation.

The baroreflex is a reflex triggered by stimulation of a baroreceptor. Baroreceptors are sensory nerve endings in the wall of the auricles of the heart, vena cava, aortic arch and carotid sinus, that are sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus form part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Stimulating the sympathetic and parasympathetic nervous systems can have effects other than on heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. Parasympathetic stimulation via the vagus nerve can also secrete insulin. The functions associated with the sympathetic and parasympathetic nervous systems are many and can be complexly integrated with each other.

Neural stimulation can be used to stimulate nerve traffic or inhibit nerve traffic. Thus, for example, a parasympathetic response can be elicited by providing neural stimulation to a parasympathetic nerve target to stimulate parasympathetic activity and/or by providing neural stimulation to a sympathetic nerve target to inhibit sympathetic activity. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic have been proposed. According to various embodiments of the present subject matter, sympathetic neural targets include, but are not limited to, a sympathetic column in a spinal cord and cardiac post-ganglionic sympathetic neurons. According to various embodiments of the present subject matter, parasympathetic neural targets include, but are not limited to, a vagus nerve, a baroreceptor, and a cardiac fat pad.

Diabetic Therapy Embodiments

FIG. 1A illustrates an embodiment of a system 100A for delivering diabetic therapy. The illustrated system includes a diabetic therapy delivery system 101A to provide a therapy for a diabetic patient. One therapy example includes a therapy to reduce the workload of the heart. Specific examples for reducing the workload of the heart are provided below with respect to FIG. 1B. Another therapy example includes an anti-arrhythmia therapy. The anti-arrhythmia therapy can be triggered upon the detection of an arrhythmia to restore a normal sinus rhythm or can be triggered upon detection of precursors of an arrhythmia as part of a prophylactic treatment to prevent the arrhythmia from occurring. Various antiarrhythmia therapies provide vagal stimulation or provide other neural stimulation to another neural target such as a cardiac fat pad. Another therapy example includes a hypertension therapy. Various hypertension therapies provide vagal stimulation or stimulate a baroreceptor to reduce blood pressure. Other therapy examples include a treatment to reduce a risk of an MI, a therapeutic treatment after MI to reduce infarct size, and a treatment to reduce sudden cardiac death (SCD); and various embodiments deliver these therapies using an appropriate vagal stimulation therapy. Another therapy example involves stimulation to secrete insulin, such as may be realized by an appropriate vagal stimulation therapy according to various embodiments. The following applications are herein incorporated by reference in their entirety: US Patent Application Pub. No. 20050149128, filed Dec. 24, 2003 and entitled "Baroreflex Stimulation System To Reduce Hypertension," U.S. application Ser. No. 11/099, 266, filed Apr. 5, 2005 and entitled "System To Treat AV-Conducted Ventricular Tachyarrhythmia," and U.S. application Ser. No. 11/077,583, filed Mar. 11, 2005 and entitled "Neural Stimulation System For Cardiac Fat Pads."

The illustrated embodiment 100A also includes therapy inputs 102A for the therapy delivery system 101A. Various embodiments use a poor glucose control input 103A and a rest/low physical activity input 104A to determine when it is appropriate to provide the diabetic therapy. For example, if the patient is experiencing poor glucose control, the diabetic therapy is delivered during periods of rest or low physical activity, such as periods of sleeping, lying down, sitting or eating. A glucose monitor (GM) 105A can be used to determine if glucose control is poor. The GM can be an implantable device or an external device such as a home glucose monitor. The GM is adapted to communicate with the therapy delivery system. The communication may occur wirelessly or using a hardwired connection. For example, wireless communication may include inductive telemetry, radiofrequency (RF) communication, and ultrasound communication. Poor glucose control may be derived from a trended heart rate 106A. Various embodiments provide a therapy control feedback, illustrated by the dotted lines 108A, for use in titrating the diabetic therapy. For example, a trended heart rate and/or a glucose monitor parameter can be used to determine the efficacy of the diabetic therapy. The glucose monitor can provide appropriate feedback to titrate the therapy, such as a therapy to secrete insulin, to maintain a blood sugar level within a desired range. Additionally, various embodiments detect whether the patient experiences bradycardia 109A, and titrate the intensity of the diabetic therapy to terminate the bradycardia episode and/or provide bradycardia support pacing as needed. Those of ordinary skill in the art will understand, upon reading and comprehending this disclosure, how to provide these therapy inputs. For example, various embodiments use one or more of an activity sensor 110A, posture sensor 111A or timer 112A to determine periods of rest or low physical activity for delivering the diabetic therapy. Heart rate sensor(s) 113A and detected nerve traffic sensor(s) 114A may also be used to indicate periods of activity.

Figure 1B:
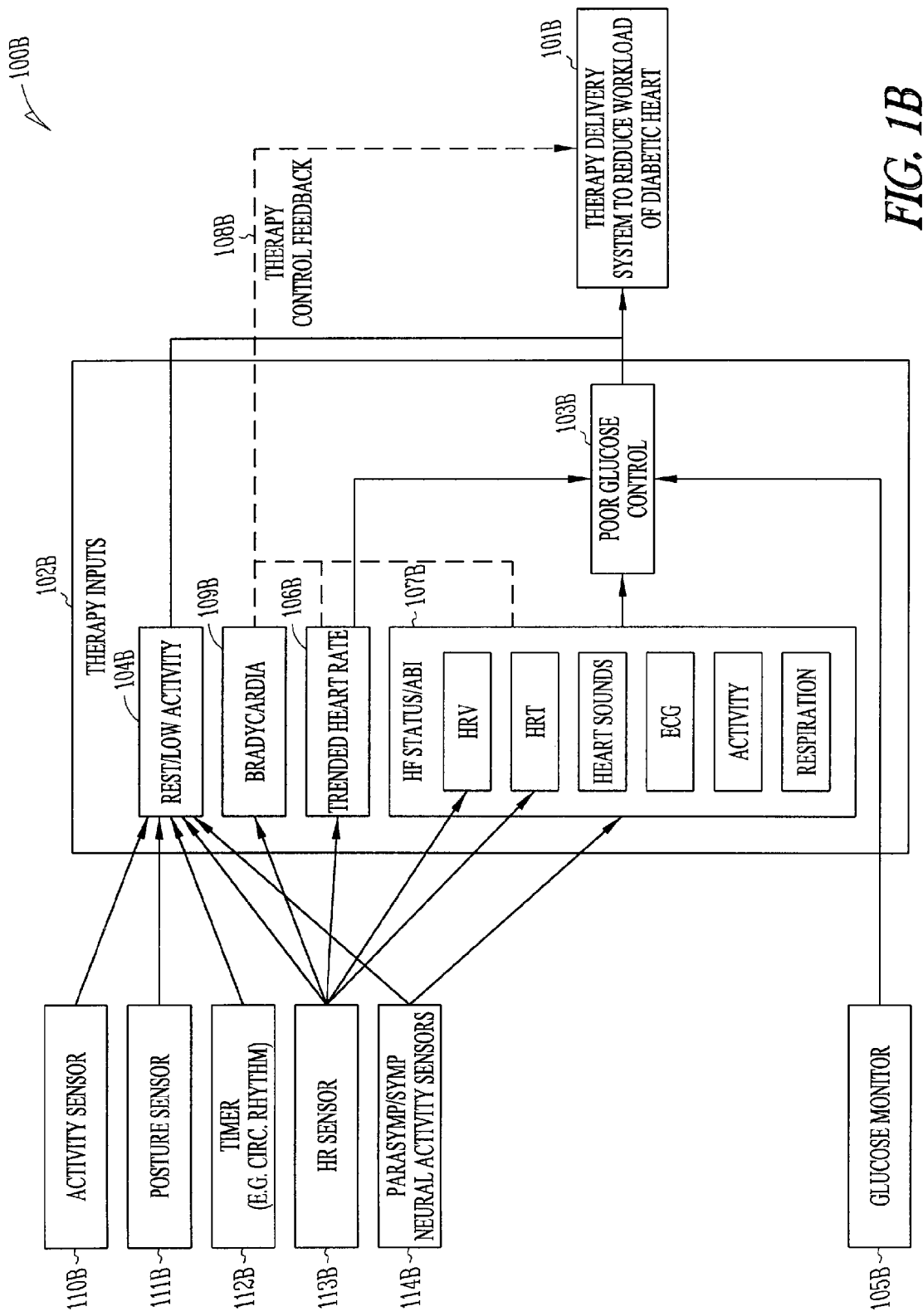
FIG. 1B illustrates an embodiment of a system for delivering therapy to reduce the workload of a diabetic heart.

FIG. 1B illustrates an embodiment of a system 100B for delivering therapy to reduce the workload of a diabetic heart. The illustrated system 100B includes a therapy delivery system 101B to selectively reduce the workload of the diabetic heart. Various system embodiments include a neural stimulation system to stimulate a neural target to reduce the heart rate when the diabetic patient is experiencing poor glucose control. Other system embodiments to unload the diabetic heart can be used. For example, drug pumps may also be used to selectively slow the heart. In an embodiment, neural stimulation, such as vagal nerve stimulation, is applied to reduce ventricular contractility (negative inotropic effect) and lower the expended myocardial energy as the contractions are less forceful. An embodiment applies neural stimulation (e.g. stimulation to elicit a parasympathetic response) to reduce cardiac sympathetic nerve activity and norepinephrine release, which can activate hypertrophy or muscle-building activity This muscle-building activity takes myocardial energy. Vagal stimulation, for example, can reduce catecholamine levels to attenuate ventricular remodeling. An embodiment applies neural stimulation, such as vagal nerve stimulation, to induce coronary artery vasodilation to improve myocardial blood flow and oxygenation to reduce myocardial anaerobic metabolism due to poor coronary circulation and ischemia associated with diabetic heart disease. An embodiment applies neural stimulation to reduce blood pressure, which reduces workload. For example, stimulation of baroreceptors, the carotid sinus, or aortic arch plexus can lower blood pressure. The vasodilation of the aorta and other peripheral arteries lower arterial peripheral resistance and lowers left ventricular systolic pressures, thus reducing workload. An embodiment applies neural stimulation, such as vagal nerve stimulation, to shift myocardial metabolism from fatty acid metabolism to glucose metabolism, which is more energy efficient. Acetylocholine binding to muscarinic receptors in the heart can stimulate the cardioprotective pathways mediated by AKT, which in turn activates GLUT4 receptors that facilitate glucose uptake and glucose metabolism by the myocytes. Stimulation (e.g. vagal nerve stimulation) that stimulates insulin release promotes glucose uptake and glucose metabolism by the myocytes. Various embodiments dispense drugs via implanted drug pumps to cause vasodilation and reduce heart workload. Various embodiments reduce the heart's work load by applying pacing pulses to the myocardium.

The illustrated embodiment 100B also includes therapy inputs 102B for the therapy delivery system 101B. Various embodiments use a poor glucose control input 103B and a rest/low physical activity input 104B to determine when it is appropriate to reduce the workload of the diabetic heart. For example, if the patient is experiencing poor glucose control, the diabetic therapy is delivered during periods of rest or low physical activity, such as periods of sleeping, lying down, sitting or eating.

Various embodiments determine that glucose control is poor using a glucose monitor (GM) 105B. The GM can be an implantable device or an external device such as a home glucose monitor. The GM is adapted to communicate with the therapy delivery system. The communication may occur wirelessly or using a hardwired connection. For example, wireless communication may include inductive telemetry, radiofrequency (RF) communication, and ultrasound communication. Poor glucose control may be derived from a trended heart rate 106B and/or from various HF status parameters 107B, such as HRV, HRT, heart sounds, ECG, activity and respiration. These HF status/autonomic balance indicator (ABI) parameters have been discussed above.

Various embodiments provide a therapy control feedback, illustrated by the dotted lines 108B, for use in titrating the diabetic therapy. For example, a trended heart rate and/or any HF status/ABI parameter can be used to determine the efficacy of the diabetic therapy. Additionally, various embodiments detect whether the patient experiences bradycardia 109B, and provide bradycardia support pacing and/or otherwise titrate the intensity of the diabetic therapy to terminate the bradycardia episode. Support pacing can create additional work for the heart, and the vagal effects on the heart are brief. Since the heart is expected to rapidly return to normal when the neural stimulation is removed or appropriately titrated, bradycardia support pacing over a time period of a few beats is expected to be adequate.

Those of ordinary skill in the art will understand, upon reading and comprehending this disclosure, how to provide these therapy inputs. For example, various embodiments use one or more of an activity sensor 110B, posture sensor 111B or timer 112B to determine desired periods (such as periods of rest or low physical activity) for delivering the diabetic therapy to reduce the workload of the heart. Heart rate sensor(s) 113B and detected nerve traffic sensor(s) 114B may also be used to indicate periods of activity. Heart rate sensors can also be used to detect bradycardia, trended heart rates, HRV and HRT. Neural activity sensors 114B can be used to detect parasympathetic activity and/or sympathetic activity to provide an indicator of autonomic balance, and thus provide a heart failure status indicator.

Figure 2:
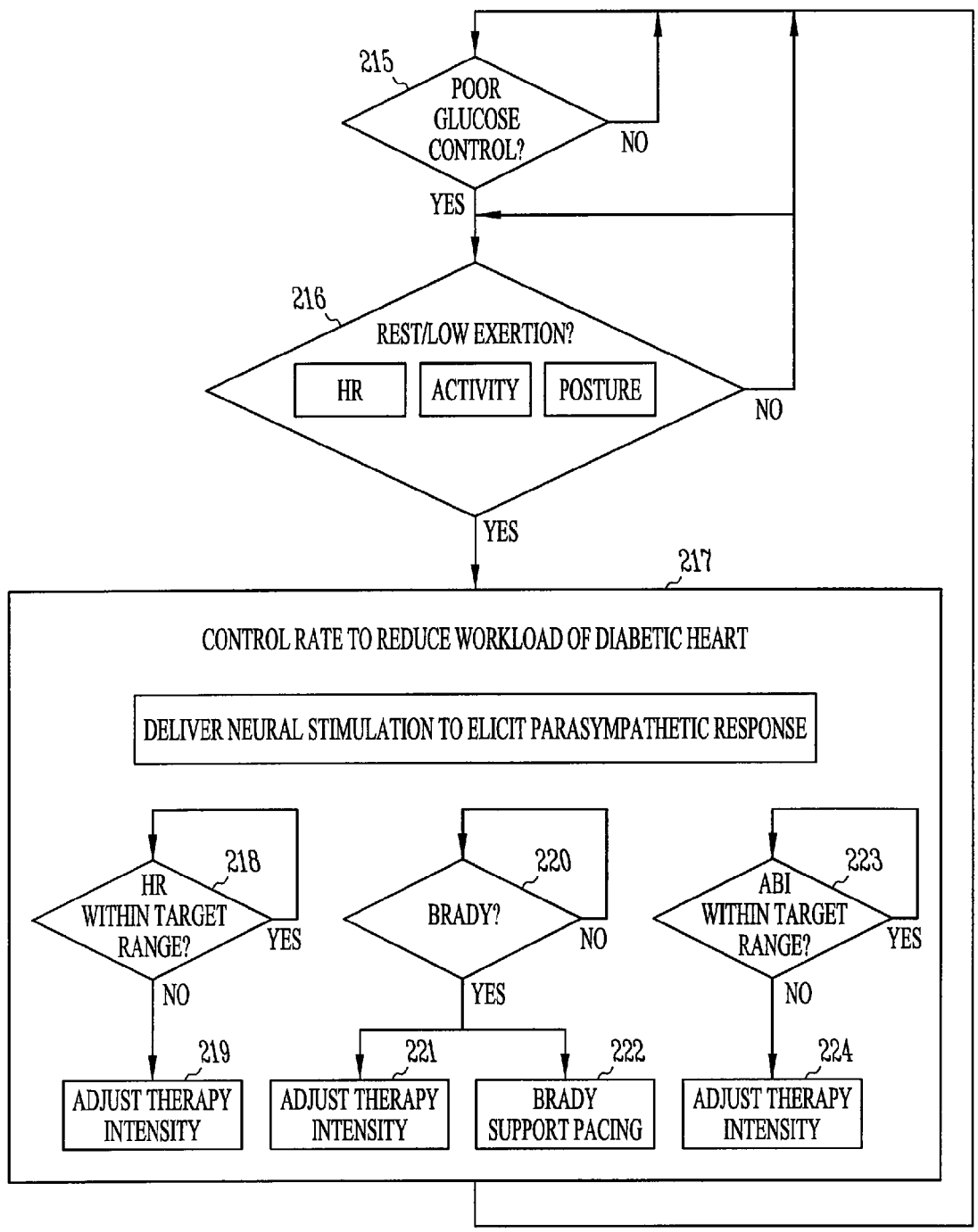
FIG. 2 illustrates a flow diagram for delivering therapy to reduce a workload of a diabetic heart, according to various embodiments.

FIG. 2 illustrates a flow diagram for delivering therapy to reduce a workload of a diabetic heart, according to various embodiments. At 215, it is determined whether the patient is experiencing poor glucose control. Various embodiments measure the glucose using a glucose monitor, or otherwise derive that the glucose is poor based on other monitored parameters (e.g. HRV, heart rate, and the like). When it is determined that the glucose control is poor, the process proceeds to 216 to determine that the patient is experiencing a time of rest or low physical exertion. Such a determination may involve heart rate measurements, activity measurements, posture measurements, and various combinations thereof. Other data inputs, such as a timer, can be used be used in determining periods of time for providing the diabetic therapy.

When it is determined that the patient is experiencing a period of rest or low physical exertion, the process proceeds to 217 to control the heart rate to reduce the workload of the diabetic heart, as it has been determined that the patient has poor glucose control and is ready for the therapy. For example, various embodiments elicit a parasympathetic response by delivering neural stimulation to a neural target that stimulates parasympathetic activity and/or inhibits sympathetic activity. Examples of neural targets include the vagus nerve, cardiac branches of the vagus nerve, and cardiac fat pads. Various embodiments selectively stimulate the vagus nerve to target a reduction in heart rate without affecting other organs, such as the pancreas, innervated by the vagus nerve. Various embodiments provide parasympathetic stimulation that also encourages insulin secretion, such as may occur with a more global stimulation of the vagus nerve. Various embodiments provide selective stimulation of the vagus nerve that encourages insulin secretion by the pancreas.

Various feedback signals can be used to control the therapy. For example, as illustrated at 218, it is determined whether the heart rate is within a target range, and the therapy intensity is adjusted at 219 to maintain the heart rate in the desired range. As illustrated at 220, it is determined whether the patient is experiencing a bradycardia episode. If bradycardia ensues the therapy intensity is appropriately adjusted at 221 and/or bradycardia support pacing is provided at 222. At 223, it is determined whether an ABI parameter (or any other HF status parameter) is within a target range, and the therapy intensity is adjusted at 224 to maintain the ABI parameter within the target range.

Device/System Embodiments

FIGS. 3A-3D illustrate various system embodiments that include a neural stimulator 325 and a glucose monitor 326.

Figure 3A:
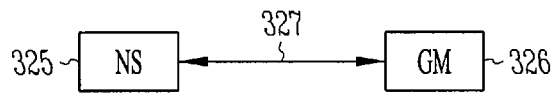
FIGS. 3A-3D illustrate various system embodiments that include a neural stimulator and a glucose monitor.
Figure 3B:
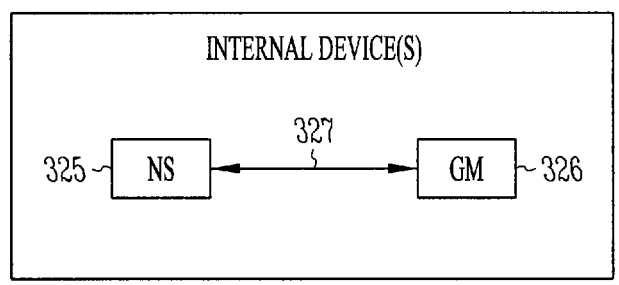
Figure 3C:
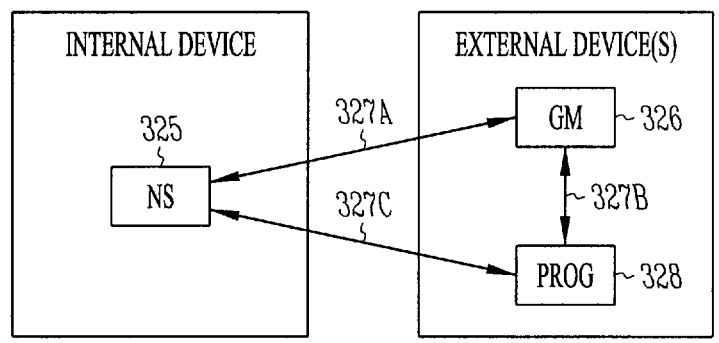
Figure 3D:
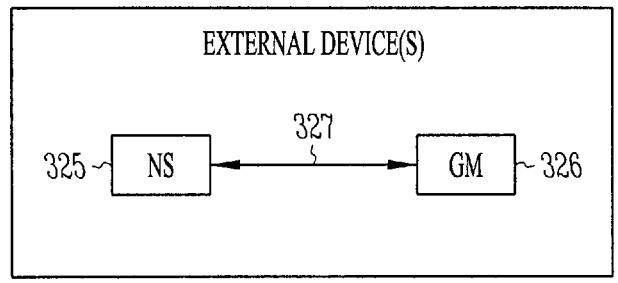

FIG. 3A generally illustrates that the neural stimulator and glucose monitor are adapted to communicate via communication channel 327. The communication can be through a tethered or hardwired connection, or through a wireless connection. The devices 325 and 326 can be separate devices or integrated devices. One of the devices 325 or 326 may also be configured to receive power from the other. FIG. 3B illustrates an embodiment wherein both the neural stimulator 325 and the glucose monitor 326 are implantable devices. FIG. 3C illustrates an embodiment in which the neural stimulator 325 is an implantable device and the glucose monitor 326 is an external device, such as a home glucose monitor for example. The glucose monitor 326 can communicate with the neural stimulator 325 via communication channel 327A, which can be an inductive telemetry channel or other wireless channel. The system illustrated in FIG. 3C also includes a programmer 328 adapted to communicate with the glucose monitor 326 via communication channel 327B and implantable neural stimulator 325 via communication channel 327C. Channel 327B can be a wired or wireless connection. Examples of a wireless connection is a Bluetooth connection or RF connection. Various wireless networking protocols can be used. Channel 327C can be an inductive telemetry channel or other wireless channel FIG. 3D illustrates an embodiment where the neural stimulator and glucose monitor are both external devices. For example, the neural stimulator can be adapted to stimulate a neural target to elicit a parasympathetic response (i.e. stimulate parasympathetic activity or inhibit sympathetic activity. The neural target can be stimulated using a transcutaneous electrode or other non-invasive electrode, and examples of neural targets that can be stimulated include an auricular branch of the vagus nerve, the peroneal nerve or other superficial peripheral nerve. Transducers, such as ultrasound transducers, can also be used to deliver neural stimulation.

Figure 4A:
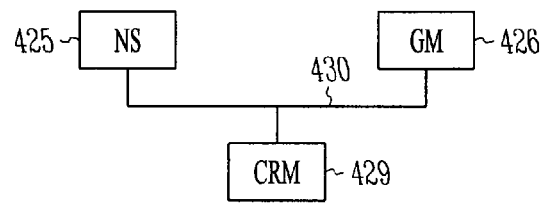
FIGS. 4A-4D illustrate various system embodiments that include a neural stimulator, a glucose monitor, and a cardiac rhythm management (CRM) device.
Figure 4B:
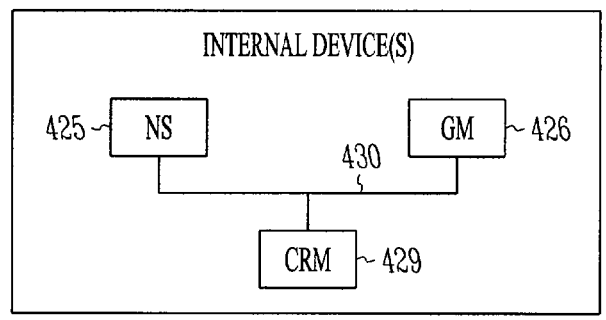
Figure 4C:
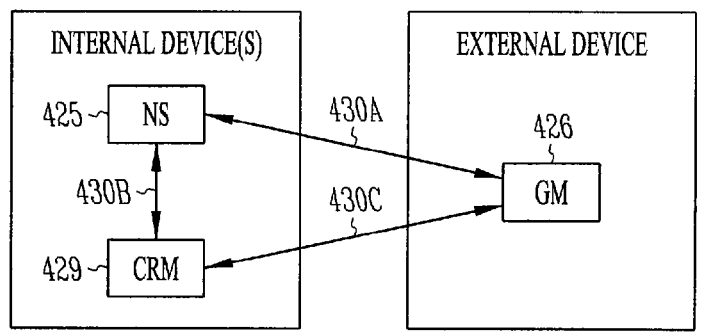
Figure 4D:
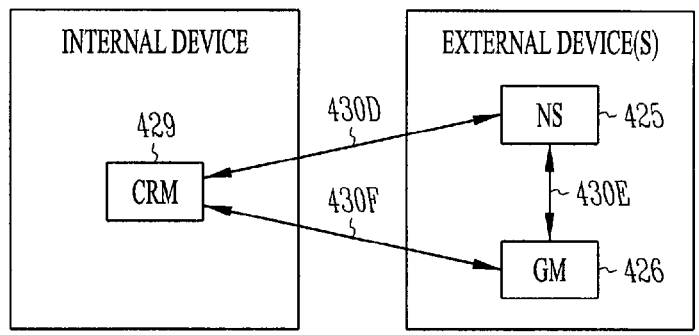

FIGS. 4A-4D illustrate various system embodiments that include a neural stimulator 425, a glucose monitor 426, and a cardiac rhythm management (CRM) device 429. As illustrated generally in FIG. 4A, the neural stimulator 425, glucose monitor 426 and CRM device 429 are adapted to communicate with each other, such as may be illustrated by communication network or bus 430. In some embodiments, one of the devices functions as a communication bridge for the other two devices. The neural stimulator 425, glucose monitor 426 and CRM device 429 can be separate devices, or two or three of the devices can be combined or integrated into a single device. FIG. 4B illustrates an embodiment where the neural stimulator 425, glucose monitor 426 and CRM device 429 are all implantable. FIG. 4C illustrates an embodiment in which the neural stimulator 425 and CRM device 429 are implantable devices, and the glucose monitor 426 is an external device. The neural stimulator 425 and CRM device 429 can be separate devices, or can be combined or integrated. Three communication channels 430A, 430B and 430C are illustrated. Those of ordinary skill will understand that one of the devices can function as a communication bridge for the other two devices, thus eliminating one of the communication channels. FIG. 4D illustrates an embodiment in which the CRM device 429 is an implantable device and the neural stimulator 425 and glucose monitor 426 are external devices. The neural stimulator 425 and glucose monitor 429 can be separate devices, or can be combined or integrated. Three communication channels 430D, 430E and 430F are illustrated. Those of ordinary skill will understand that one of the devices can function as a communication bridge for the other two devices, thus eliminating one of the communication channels.

Figure 5:
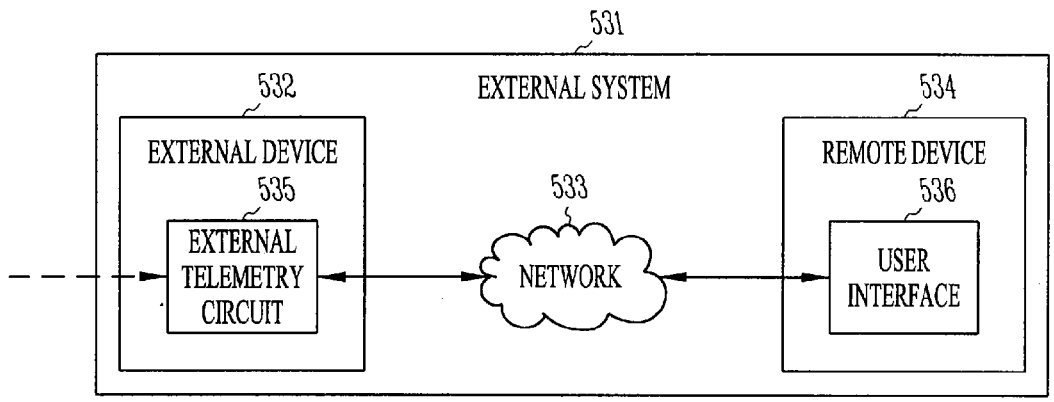
FIG. 5 is a block diagram illustrating an embodiment of an external system.

FIG. 5 is a block diagram illustrating an embodiment of an external system 531. The external system includes a programmer, in some embodiments. In the illustrated embodiment, the external system includes a patient management system. As illustrated, the external system 531 is a patient management system including an external device 532, a telecommunication network 533, and a remote device 534. External device 532 is placed within the vicinity of an implantable medical device (IMD) and includes external telemetry system 535 to communicate with the IMD. Remote device(s) 534 is in one or more remote locations and communicates with external device 532 through network 533, thus allowing a physician or other caregiver to monitor and treat a patient from a distant location and/or allowing access to various treatment resources from the one or more remote locations. The illustrated remote device 534 includes a user interface 536. According to various embodiments, the external device 532 includes a glucose monitor, a neural stimulator, a programmer or other device such as a computer, a personal data assistant or phone. The external device 532, in various embodiments, includes two devices adapted to communicate with each other over an appropriate communication channel, such as a computer and a Bluetooth enabled glucose monitor, by way of example and not limitation.

Figure 6:
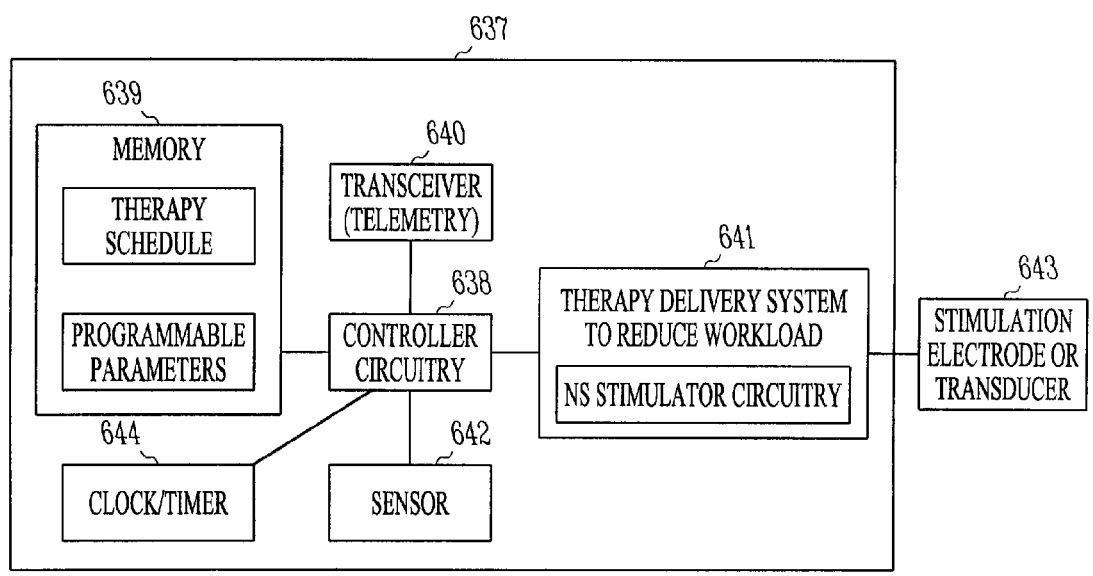
FIG. 6 illustrates an implantable medical device (IMD), according to various embodiments of the present subject matter.

FIG. 6 illustrates an implantable medical device (IMD) 637, according to various embodiments of the present subject matter. The illustrated IMD 637 provides neural stimulation signals for delivery to predetermined neural targets to provide diabetic therapy. The illustrated device includes controller circuitry 638 and memory 639. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The illustrated device further includes a transceiver 640 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes a diabetic therapy delivery system 641, such as neural stimulation circuitry. Other therapy delivery systems, such as drug delivery systems, can be used. Various embodiments of the device also includes sensor circuitry 642. Examples of sensors were provided in FIG. 1. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 643 positioned at predetermined location(s). Some embodiments use transducers to provide other types of energy, such as ultrasound, light or magnetic energy. In various embodiments, the sensor circuitry is used to detect physiological responses. Examples of physiological responses include blood pressure, cardiac activity such as heart rate, and respiration such as tidal volume and minute ventilation. The controller circuitry can control the therapy provided by system 641 using a therapy schedule in memory 639, or can compare a target range (or ranges) of the sensed physiological response(s) stored in the memory 639 to the sensed physiological response(s) to appropriately adjust the intensity of the neural stimulation/inhibition.

According to various embodiments using neural stimulation, the stimulation circuitry 641 is adapted to set or adjust any one or any combination of stimulation features. Examples of stimulation features include the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring baroreflex stimulation. Some embodiments of the neural stimulation circuitry 641 are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry 641 are adapted to generate a stimulation signal with a predetermined frequency, and are further adapted to respond to a control signal from the controller to modify the frequency of the stimulation signal.

The controller 638 can be programmed to control the neural stimulation delivered by the stimulation circuitry 641 according to stimulation instructions, such as a stimulation schedule, stored in the memory 639. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time.

Various embodiments provide diabetic heart disease therapy using neural stimulation to selectively reduce heart rate to reduce cardiac workload when poor glucose control is detected and the patient is sedentary. In various embodiments, for example, the neural target is the vagus nerve on the right side in cervical region, which enhances the ability to drive lower heart rates. Various embodiments preferentially drive efferent stimulation (e.g., with tripolar lead designed for selective stimulation) to avoid afferent-mediated side-effects. The neural stimulation can occur in continuous bursts with duration on the order of 30 seconds to 5 minutes. The neural stimulation bursts can be applied on the order of one burst per minute to one burst per hour. Shorter bursts are associated with faster duty cycles (e.g. 30 sec burst per 1 min.) and longer bursts are associated with slower duty cycles (e.g., 5 min burst per 1 hour). The stimulation pulse frequency during each burst is selected to recruit a desired heart rate response. According to various embodiments, the stimulation pulse frequency is nominally in the range of 10-30 Hz with pulse widths on the order of 0.3-1.0 ms and amplitudes on the order of 0.2-2.0 mA. Various embodiments adjust the neural stimulation intensity to target heart rate reductions on the order of 10-30%.

According to some embodiments, the controller 638 controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller 638 controls the stimulation circuitry 641 to initiate a neural stimulation session and to terminate the neural stimulation session. The burst duration of the neural stimulation session under the control of the controller 638 can be programmable. The controller may also terminate a neural stimulation session in response to an interrupt signal, such as may be generated by one or more sensed parameters or any other condition where it is determined to be desirable to stop neural stimulation.

The sensor circuitry is used to detect a physiological response. The controller 638 compares the response to a target range stored in memory, and controls the neural stimulation based on the comparison in an attempt to keep the response within the target range. The target range can be programmable.

The illustrated device includes a clock or timer 644 which can be used to execute the programmable stimulation schedule. For example, a physician can program a daily schedule of therapy based on the time of day if the glucose control is determined to be poor. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the schedule refers to the time intervals or period when the neural stimulation therapy is delivered. A schedule can be defined by a start time and an end time, or a start time and a duration. Various schedules deliver therapy periodically. According to various examples, a device can be programmed with a therapy schedule to deliver therapy from midnight to 2 AM every day, or to deliver therapy for one hour every six hours, or to delivery therapy for two hours per day, or according to a more complicated timetable. Various device embodiments apply the therapy according to the programmed schedule contingent on enabling conditions, such as poor glucose control, patient rest or sleep, low heart rate levels, and the like. The therapy schedule can also specify how the stimulation is delivered, such as continuously at the pulse frequency throughout the identified therapy period (e.g. 5 Hz pulse frequency for one hour during the delivery period), or according to a defined duty cycle during the therapy delivery period (e.g. 10 seconds per minute at 5 Hz pulse frequency for one hour per day). As illustrated by these examples, the therapy schedule is distinguishable from the duty cycle.

Figure 7:
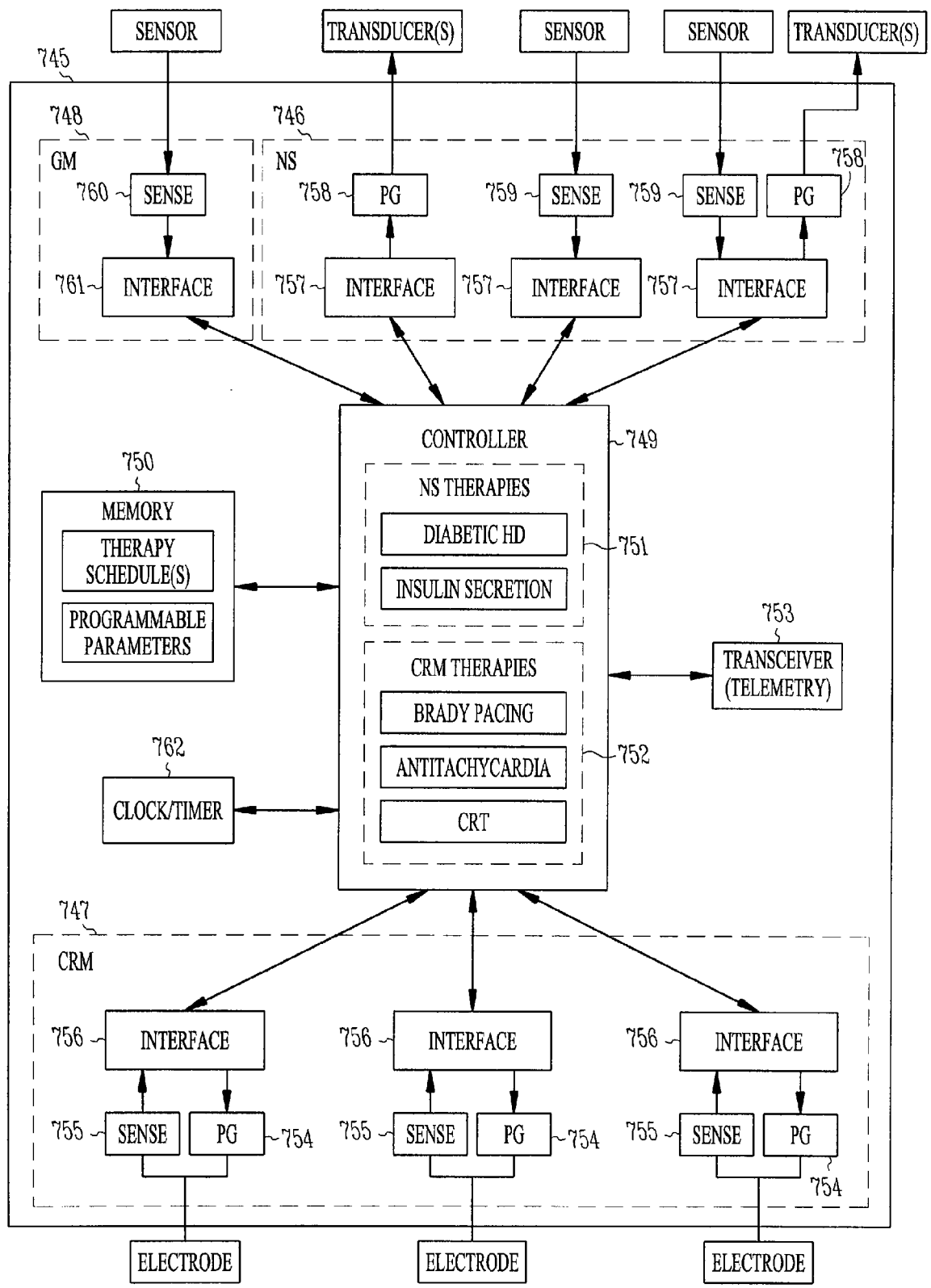
FIG. 7 illustrates an implantable medical device (IMD) having a neural stimulation (NS) component and cardiac rhythm management (CRM) component, according to various embodiments of the present subject matter.

FIG. 7 illustrates an implantable medical device (IMD) 745 having a neural stimulation (NS) component 746, a cardiac rhythm management (CRM) component 747, and a glucose monitoring component 748 according to various embodiments of the present subject matter. The illustrated device includes a controller 749 and memory 750. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 751 includes a diabetic therapy and insulin secretion therapy. Various embodiments include CRM therapies 752, such as bradycardia pacing, anti-tachycardia therapies such as ATP, defibrillation and cardioversion, and cardiac resynchronization therapy (CRT). The illustrated device further includes a transceiver 753 and associated circuitry for use to communicate with a programmer or another external or internal device. Various embodiments include a telemetry coil.

The CRM therapy section 747 includes components, under the control of the controller, to stimulate a heart and/or sense cardiac signals using one or more electrodes. The illustrated CRM therapy section includes a pulse generator 754 for use to provide an electrical signal through an electrode to stimulate a heart, and further includes sense circuitry 755 to detect and process sensed cardiac signals. An interface 756 is generally illustrated for use to communicate between the controller 749 and the pulse generator 754 and sense circuitry 755. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 746 includes components, under the control of the controller, to stimulate a neural stimulation target and/or sense parameters associated with nerve activity or surrogates of nerve activity such as blood pressure and respiration. Three interfaces 757 are illustrated for use to provide neural stimulation. However, the present subject matter is not limited to a particular number interfaces, or to any particular stimulating or sensing functions. Pulse generators 758 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 759 are used to detect and process signals from a sensor, such as a sensor of nerve activity, blood pressure, respiration, and the like. The interfaces 757 are generally illustrated for use to communicate between the controller 749 and the pulse generator 758 and sense circuitry 759. Each interface, for example, may be used to control a separate lead. Various embodiments of the NS therapy section only includes a pulse generator to stimulate a neural target. The glucose monitor section 748 includes sensor circuitry 760 and an interface 761 to communicate between the controller 749 and the sensor circuitry 760. The illustrated device further includes a clock/timer 762, which can be used to deliver the programmed therapy according to a programmed stimulation protocol and/or schedule.

Figure 8:
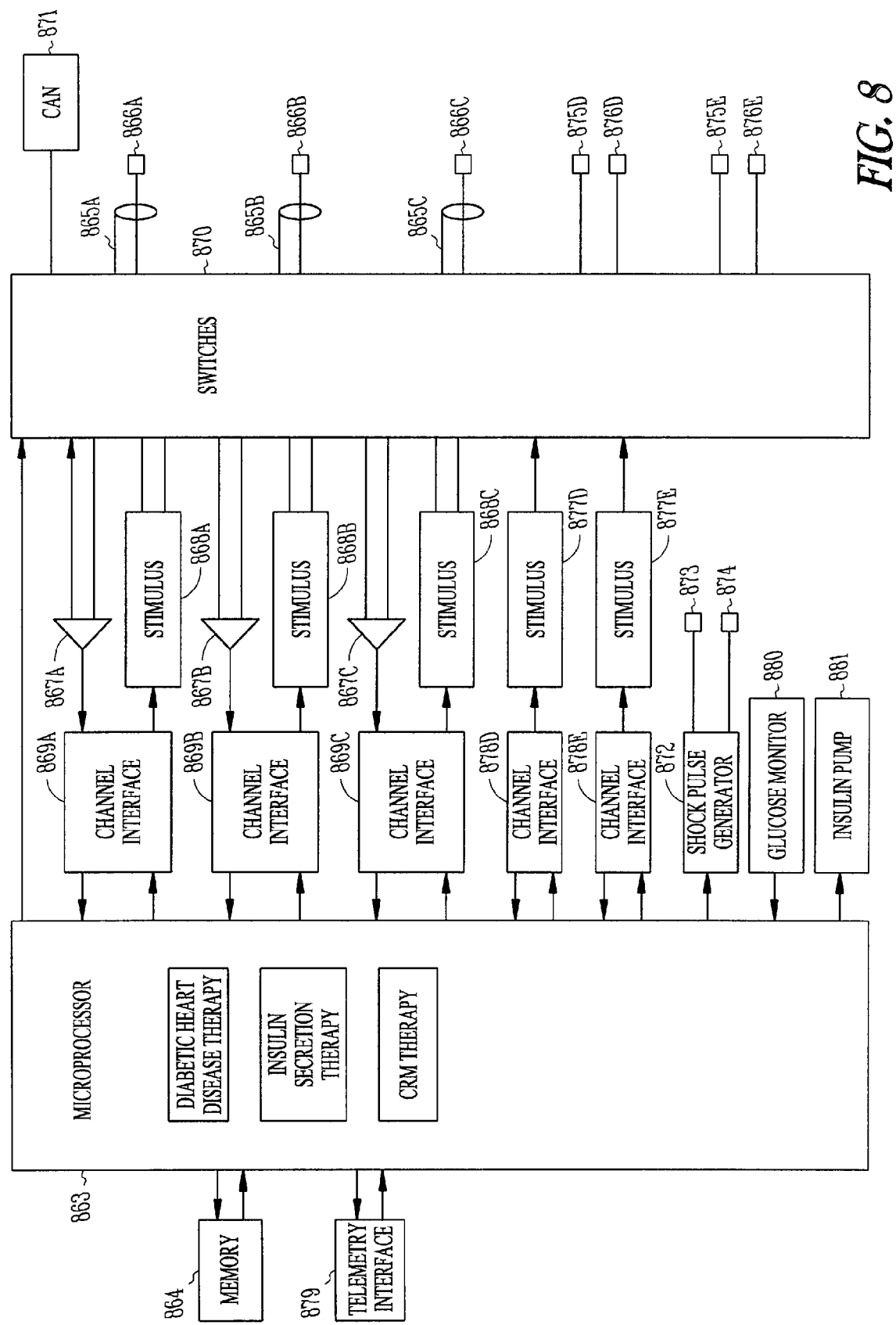
FIG. 8 shows a system diagram of an embodiment of a microprocessor-based implantable device, according to various embodiments.

FIG. 8 shows a system diagram of an embodiment of a microprocessor-based implantable device, according to various embodiments. The controller of the device is a microprocessor 863 which communicates with a memory 864 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 865A-C and tip electrodes 866A-C, sensing amplifiers 867A-C, pulse generators 868A-C, and channel interfaces 869A-C. Each channel thus includes a pacing channel made up of the pulse generator connected to the electrode and a sensing channel made up of the sense amplifier connected to the electrode. The channel interfaces 869A-C communicate bidirectionally with the microprocessor 863, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 870 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 871 or an electrode on another lead serving as a ground electrode. A shock pulse generator 872 is also interfaced to the controller for delivering a defibrillation shock via a pair of shock electrodes 873 and 874 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 875D and a second electrode 876D, a pulse generator 877D, and a channel interface 878D, and the other channel includes a bipolar lead with a first electrode 875E and a second electrode 876E, a pulse generator 877E, and a channel interface 878E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 879 connected to the microprocessor, which can be used to communicate with an external device. The device also includes a glucose monitor 880 adapted to communicate with the microprocessor 863. The illustrated microprocessor 863 is capable of performing neural stimulation therapy routines and myocardial (CRM) stimulation routines. Examples of NS therapy routines include a diabetic therapy and an insulin secretion therapy. The insulin secretion therapy may also dispense insulin via the insulin pump 881. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 9:
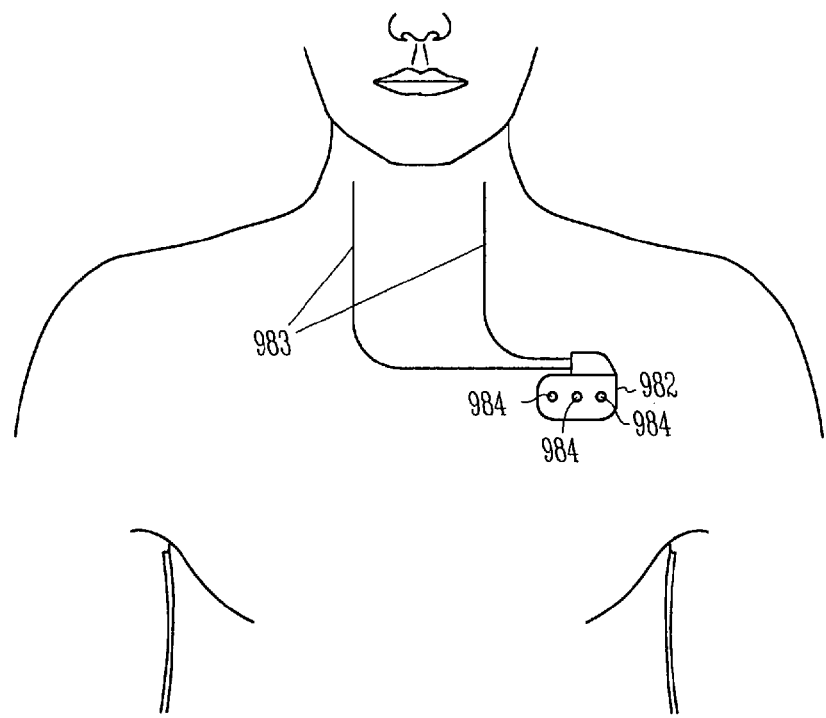
FIG. 9 illustrates a system embodiment in which an IMD is placed subcutaneously or submuscularly in a patient's chest with lead(s) positioned to stimulate a vagus nerve.

FIG. 9 illustrates a system embodiment in which an IMD 982 is placed subcutaneously or submuscularly in a patient's chest with lead(s) 983 positioned to stimulate a vagus nerve. According to various embodiments, neural stimulation lead(s) 983 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes on the housing of the device. These ECG electrodes 984 are capable of being used to detect heart rate, for example.

Figure 10:
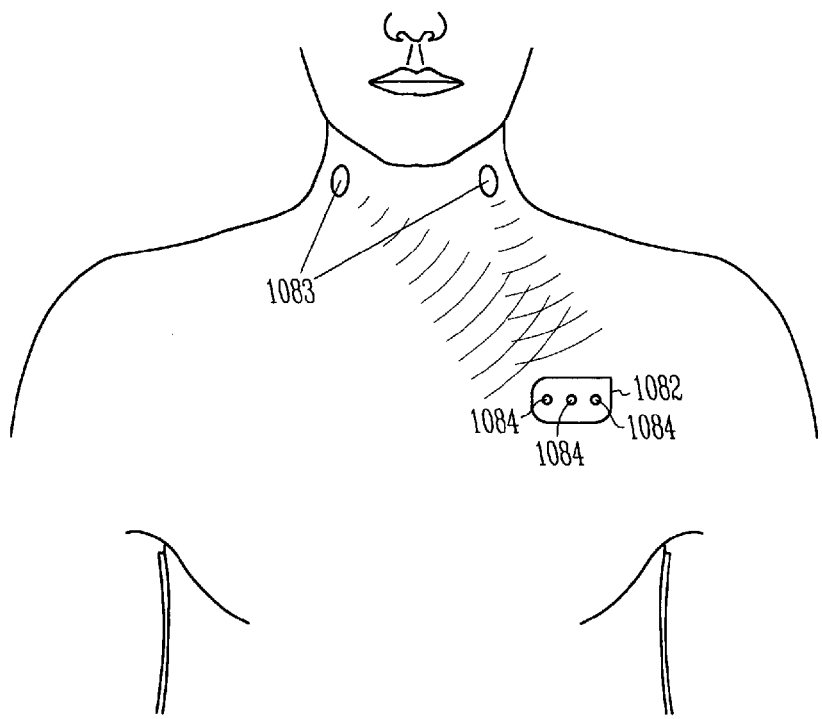
FIG. 10 illustrates a system embodiment that includes an implantable medical device (IMD) with satellite electrode(s) positioned to stimulate at least one neural target.

FIG. 10 illustrates a system embodiment that includes an implantable medical device (IMD) 1082 with satellite electrode(s) 1083 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 1084 are capable of being used to detect heart rate, for example.

Figure 11:
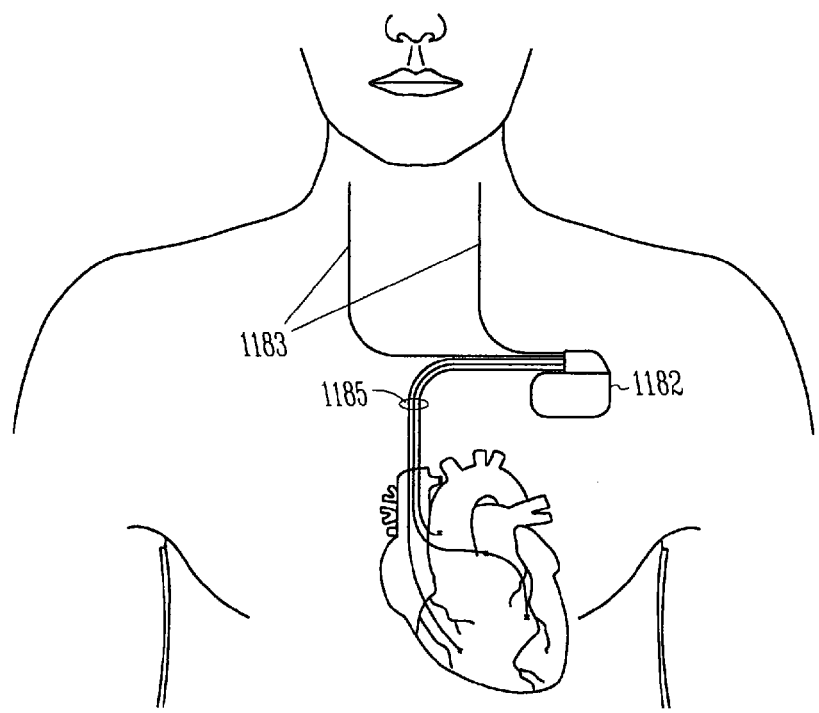
FIG. 11 illustrates an IMD placed subcutaneously or submuscularly in a patient's chest with lead(s) positioned to provide a CRM therapy to a heart, and with lead(s) positioned to stimulate and/or inhibit neural traffic in a vagus nerve, by way of example and not by way of limitation, according to various embodiments.

FIG. 11 illustrates an IMD 1182 placed subcutaneously or submuscularly in a patient's chest with lead(s) 1185 positioned to provide a CRM therapy to a heart, and with lead(s) 1183 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 12:
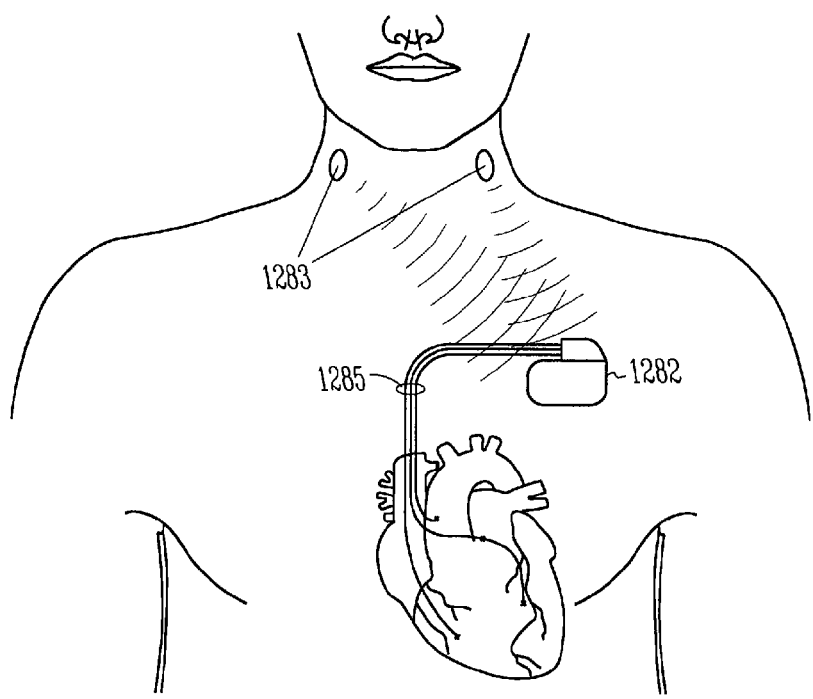
FIG. 12 illustrates an IMD with lead(s) positioned to provide a CRM therapy to a heart, and with satellite transducers positioned to stimulate/inhibit a neural target, according to various embodiments.

FIG. 12 illustrates an IMD 1282 with lead(s) 1285 positioned to provide a CRM therapy to a heart, and with satellite transducers 1283 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Other Therapies

Embodiments of the present subject matter use neural stimulation to slow heart rate and reduce the workload of the heart of a diabetic patient when the glucose control for the patient is poor. Other neural stimulation therapies include neural stimulation therapies for heart failure, for blood pressure control such as to treat hypertension, for respiratory problems such a sleep disordered breathing, for cardiac rhythm management, for myocardial infarction and ischemia, for epilepsy, for depression, for pain, for migraines, for eating disorders and obesity, and for movement disorders. This listing of other neural stimulation therapies is not intended to be an exhaustive listing. These neural stimulation therapies can be combined with diabetic therapy.

Various embodiments combine diabetic therapy with a myocardial stimulation therapy and/or other neural stimulation therapies. Some of these therapies are discussed below.

A pacemaker is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues.

In order to treat these problems, implantable CRT devices have been developed that provide appropriately timed electrical stimulation to one or more heart chambers in an attempt to improve the coordination of atrial and/or ventricular contractions. Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace. CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle in a manner which causes a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

One neural stimulation therapy involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity. When delivered in conjunction with CRT, such modulation of autonomic activity acts synergistically to reverse or prevent cardiac remodeling. Increased sympathetic nervous system activity following ischemia often results in increased exposure of the myocardium to epinephrine and norepinephrine. These catecholamines activate intracellular pathways within the myocytes, which lead to myocardial death and fibrosis. Stimulation of the parasympathetic nerves (vagus) inhibits this effect. According to various embodiments, the present subject matter selectively activates the vagal cardiac nerves in addition to CRT in heart failure patients to protect the myocardium from further remodeling and arrhythmogenesis. Other potential benefits of stimulating vagal cardiac nerves in addition to CRT include reducing inflammatory response following myocardial infarction, and reducing the electrical stimulation threshold for defibrillating. For example, when a ventricular tachycardia is sensed, vagal nerve stimulation is applied, and then a defibrillation shock is applied. The vagal nerve stimulation allows the defibrillation shock to be applied at less energy. Also, parasympathetic stimulation may terminate an arrhythmia or otherwise increase the effectiveness of an anti-arrhythmia treatment.

One of ordinary skill in the art will understand that the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions there of, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system for providing therapy to a patient, comprising: a glucose control input configured to receive an indicator that the patient has poor glucose control and a low physical activity input configured to receive an indicator that the patient is experiencing low exertion, wherein the poor glucose control indicates that a heart is a diabetic heart that is less efficient in producing adenosine triphosphate (ATP) energy molecules than a healthy heart, and wherein the low exertion indicates that the patient is in a period of rest; and
a diabetic electrical therapy delivery system configured to reduce a workload of the diabetic heart, wherein reducing the workload of the diabetic heart reduces demand for ATP energy molecules, wherein the diabetic therapy delivery system is connected to the glucose control input and the low physical activity input and configured to use the glucose control input to determine that the patient has poor glucose control and use the low physical activity input to determine that the patient is experiencing low exertion, wherein the diabetic therapy delivery system is configured to reduce the workload of the diabetic heart only on condition that the diabetic therapy delivery system determines that the patient has poor glucose control and is experiencing low exertion.

2. The system of claim 1, wherein the diabetic electrical therapy delivery system is further configured to deliver an anti-arrhythmia therapy.

3. The system of claim 1, wherein the diabetic electrical therapy delivery system is further configured to deliver a neural stimulation therapy adapted to provide a hypertension therapy.

4. The system of claim 1, wherein the diabetic electrical therapy delivery system is further configured to deliver a neural stimulation therapy adapted to reduce a risk of myocardial infarction.

5. The system of claim 1, wherein the diabetic electrical therapy delivery system is further configured to deliver a neural stimulation therapy adapted to be applied after a myocardial infarction to reduce an infarct area.

6. The system of claim 1, wherein the diabetic electrical therapy delivery system is further configured to deliver a neural stimulation therapy adapted to reduce a risk of sudden cardiac death.

7. The system of claim 1, wherein the diabetic electrical therapy delivery system is further configured to deliver an electrical therapy adapted to secrete insulin.

8. The system of claim 7, wherein the electrical therapy adapted to secrete insulin includes a neural stimulation therapy.

9. The system of claim 8, wherein the neural stimulation therapy is adapted to respond to the glucose control input to adjust or stop the neural stimulation therapy when a glucose level reaches a high level.

10. The system of claim 1, wherein the diabetic electrical therapy delivery system is configured to reduce ventricular contractility to reduce the workload of the diabetic heart.

11. The system of claim 1, wherein the diabetic electrical therapy delivery system is configured to reduce norepinephrine release to attenuate ventricular remodeling, reducing the workload of the diabetic heart.

12. The system of claim 1, wherein the diabetic electrical therapy delivery system is configured to induce coronary artery vasodilation to reduce the workload of the diabetic heart.

13. The system of claim 1, wherein the diabetic electrical therapy delivery system is configured to lower arterial peripheral resistance to reduce the workload of the diabetic heart.

14. The system of claim 1, wherein the diabetic electrical therapy delivery system is configured to stimulate insulin release to promote glucose uptake and metabolism to reduce the workload of the diabetic heart.

15. The system of claim 1, wherein the diabetic electrical therapy delivery system is configured to stimulate myocardia to reduce the workload of the diabetic heart.

16. The system of claim 1, wherein the diabetic electrical therapy delivery system is configured to slow a heart rate of the diabetic heart to reduce the workload of the diabetic heart.

17. The system of claim 1, wherein the diabetic electrical therapy delivery system includes a neural stimulation therapy system adapted to stimulate a neural target to elicit a parasympathetic response to reduce the workload of the diabetic heart.

18. The system of claim 17, wherein the neural stimulation therapy system is adapted to stimulate a vagus nerve.

19. The system of claim 18, wherein the neural stimulation therapy system is responsive to the glucose control input and the low physical activity input to selectively stimulate the vagus nerve to slow heart rate.

20. The system of claim 18, wherein the neural stimulation therapy system is responsive to the glucose control input and the low physical activity input to stimulate the vagus nerve to secrete insulin.

21. The system of claim 18, wherein the neural stimulation therapy system is responsive to the glucose control input and the low physical activity input to stimulate the vagus nerve to slow heart rate and secrete insulin.

22. The system of claim 1, wherein the glucose control input, the low physical activity input, and the diabetic electrical therapy delivery system are contained within at least one external device.

23. The system of claim 1, wherein the glucose control input is in an external glucose monitor, and the diabetic electrical therapy delivery system is in an external neural stimulation device, the neural stimulation device and the glucose monitor being adapted to communicate.

24. The system of claim 23, further comprising an implantable cardiac rhythm management (CRM) device, the CRM device being adapted to communicate to the external glucose monitor, the external neural stimulation device, or both the external glucose monitor and the external neural stimulation device.

25. The system of claim 23, wherein the external neural stimulation device is adapted to stimulate a neural target using a transcutaneous electrode.

26. The system of claim 1, wherein the glucose control input is derived using a heart failure status parameter.

27. The system of claim 26, wherein the heart failure status parameter includes a heart rate variability (HRV) parameter, a heart rate turbulence (HRT) parameter, a heart sound parameter, an ECG feature, an activity parameter or a respiration feature.

28. The system of claim 1, wherein the glucose control input is derived using a trended heart rate.

29. The system of claim 1, wherein the low physical activity input is derived using an activity sensor, a posture sensor, or a timer.

30. The system of claim 1, wherein the diabetic electrical therapy delivery system is adapted to be responsive to a therapy control feedback.

31. The system of claim 30, wherein the therapy control feedback includes a detected bradycardia.

32. The system of claim 30, wherein the therapy control feedback includes a measured glucose level.

33. A method, comprising:
determining if a diabetic patient has poor glucose control, wherein the poor glucose control indicates that a heart is a diabetic heart that is less efficient in producing adenosine triphosphate (ATP) energy molecules than a healthy heart;
determining when the diabetic patient is experiencing low physical exertion, wherein the low exertion indicates that the patient is in a period of rest; and
delivering diabetic electrical therapy to reduce a workload of the diabetic heart only on condition that it is determined that the diabetic patient has poor glucose control and is experiencing low physical exertion, wherein reducing the workload of the diabetic heart reduces demand for ATP energy molecules.

34. The method of claim 33, further comprising delivering an anti-arrhythmia therapy, delivering a hypertension therapy, reducing a risk of myocardial infarction, applying the diabetic therapy after a myocardial infarction to reduce an infarct area, or reducing a risk of sudden cardiac death.

35. The method of claim 33, further comprising delivering or secreting insulin to promote glucose uptake and metabolism to reduce the workload of the diabetic heart.

36. The method of claim 33, wherein determining when the diabetic patient is experiencing low physical exertion includes determining when the diabetic patient is sleeping, determining when the diabetic patient is lying down, or determining when the diabetic patient is sitting.

37. The method of claim 33, wherein delivering diabetic electrical therapy to reduce a workload of a diabetic heart includes delivering neural stimulation to elicit a parasympathetic response, including delivering neural stimulation to stimulate parasympathetic nerve activity or delivering neural stimulation to inhibit sympathetic nerve activity.

38. The method of claim 37, wherein delivering neural stimulation to elicit the parasympathetic response includes delivering neural stimulation to slow a heart rate.

39. The method of claim 38, wherein delivering neural stimulation to slow the heart rate includes delivering neural stimulation to a vagus nerve.

40. The method of claim 39, wherein delivering neural stimulation to the vagus nerve includes stimulating insulin secretion.

41. The method of claim 39, wherein delivering neural stimulation to the vagus nerve includes selectively stimulating the vagus nerve to slow heart rate.

42. The method of claim 33, wherein delivering diabetic electrical therapy includes delivering neural stimulation to secrete insulin, delivering neural stimulation to reduce ventricular contractility, delivering neural stimulation to reduce norepinephrine release to attenuate ventricular remodeling, delivering neural stimulation to induce coronary artery vasodilation, delivering neural stimulation to lower arterial peripheral resistance, or delivering neural stimulation to stimulate insulin release to promote glucose uptake and metabolism.

* * * * *